(12) United States Patent
Henry et al.

(10) Patent No.: US 9,479,859 B2
(45) Date of Patent: Oct. 25, 2016

(54) CONCHA-FIT ELECTRONIC HEARING PROTECTION DEVICE

(71) Applicant: 3M INNOVATIVE PROPERTIES COMPANY, St. Paul, MN (US)

(72) Inventors: Paul D. Henry, Carmel, IN (US); Michael J. Pescetto, Spring, TX (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 14/082,670

(22) Filed: Nov. 18, 2013

(65) Prior Publication Data

US 2015/0139474 A1    May 21, 2015

(51) Int. Cl.
| | | |
|---|---|---|
| *H04R 25/00* | (2006.01) | |
| *H04R 1/10* | (2006.01) | |
| *A61F 11/08* | (2006.01) | |
| *A61F 11/14* | (2006.01) | |

(52) U.S. Cl.
CPC ............. *H04R 1/1058* (2013.01); *A61F 11/08* (2013.01); *H04R 1/1016* (2013.01); *A61F 2011/145* (2013.01)

(58) Field of Classification Search
USPC ................................................. 381/322, 328
See application file for complete search history.

(56) References Cited

U.S. PATENT DOCUMENTS

| | | | |
|---|---|---|---|
| 2,188,591 A * | 1/1940 | Carlson ................ | H04R 25/652 181/132 |
| 2,763,334 A | 9/1956 | Starkey | |
| 2,971,065 A | 2/1961 | Busse | |
| 3,097,059 A | 7/1963 | Hoffman | |
| 3,312,789 A * | 4/1967 | Lewis .................. | H04R 25/456 381/322 |
| 3,783,201 A * | 1/1974 | Weiss ..................... | H04R 25/60 381/324 |
| 4,537,187 A | 8/1985 | Scott | |
| 4,550,227 A * | 10/1985 | Topholm ................ | H04R 25/60 381/322 |
| 4,702,238 A | 10/1987 | Scott | |
| 4,736,435 A | 4/1988 | Yokoyama | |
| 4,878,560 A * | 11/1989 | Scott .................... | H04R 1/1016 181/130 |
| 4,880,076 A * | 11/1989 | Ahlberg ............... | H04R 25/656 181/130 |
| 5,659,156 A | 8/1997 | Mauney | |
| 6,122,388 A | 9/2000 | Feldman | |
| 6,704,429 B2 | 3/2004 | Lin | |
| 6,830,124 B2 | 12/2004 | Chiang | |
| 7,025,061 B2 | 4/2006 | Haussmann | |
| 7,027,608 B2 * | 4/2006 | Fretz ..................... | H04R 25/65 381/322 |
| 7,394,910 B2 * | 7/2008 | Smith .................. | H04R 1/1016 381/322 |
| 7,916,884 B2 | 3/2011 | Kah, Jr. | |
| 8,065,118 B2 | 11/2011 | Mcbagonluri | |

(Continued)

FOREIGN PATENT DOCUMENTS

| | | |
|---|---|---|
| CA | 2188260 | 11/1995 |
| EP | 1652366 | 5/2006 |

(Continued)

OTHER PUBLICATIONS

Audrey Jourdan, "Phonak makes a splash with its new water and dirt resistant portfolio", Oct. 19, 2011.*
Audrey Jourdan, "Phonak Makes a Splash With Its New Water and Dirst Resistance Portfolio", Oct. 19, 2011.*

(Continued)

*Primary Examiner* — Davetta W Goins
*Assistant Examiner* — Amir Etesam

(57) ABSTRACT

A concha-fit electronic hearing protection device including an eartip and an earpiece body. When the device is fitted in the ear of a user, the eartip externally occludes the ear canal and the earpiece body internally occludes the eartip.

22 Claims, 2 Drawing Sheets

(56) References Cited

U.S. PATENT DOCUMENTS

| | | |
|---|---|---|
| 8,130,942 B2 | 3/2012 | Howes |
| 8,270,648 B2 | 9/2012 | Murozaki |
| 8,281,791 B2 | 10/2012 | Mance |
| 8,391,526 B2 | 3/2013 | Dahl |
| 2006/0067556 A1 | 3/2006 | Bailey |
| 2009/0141923 A1 | 6/2009 | Smith |
| 2009/0252362 A1 | 10/2009 | Ooi |
| 2011/0019849 A1 | 1/2011 | Nielsen |
| 2011/0075871 A1 | 3/2011 | Fretz |
| 2011/0103605 A1 | 5/2011 | Killion |
| 2011/0280423 A1 | 11/2011 | Nielsen |
| 2012/0140963 A1* | 6/2012 | Larsen .................. H04R 25/30 381/315 |
| 2012/0140967 A1 | 6/2012 | Aubert |
| 2012/0237068 A1 | 9/2012 | Fretz |
| 2012/0269376 A1 | 10/2012 | Matsuo |

FOREIGN PATENT DOCUMENTS

| | | |
|---|---|---|
| EP | 2299730 | 3/2011 |
| GB | 448430 | 6/1936 |
| WO | WO 01-50813 | 7/2001 |
| WO | WO 02-052890 | 7/2002 |
| WO | WO 2007/014950 | 2/2007 |
| WO | WO 2009/004395 | 1/2009 |
| WO | WO 2010-096884 | 9/2010 |

OTHER PUBLICATIONS

U.S. Appl. No. 29/473,001, Henry et al., entitled Hearing Protector windscreen, filed Nov. 18, 2013.
U.S. Appl. No. 29/473,006, Henry et al., entitled Hearing Protector Housing, filed Nov. 18, 2013.
International Search Report for PCT/US2014/060105, mailed Dec. 22, 2014, 4 pp.

* cited by examiner

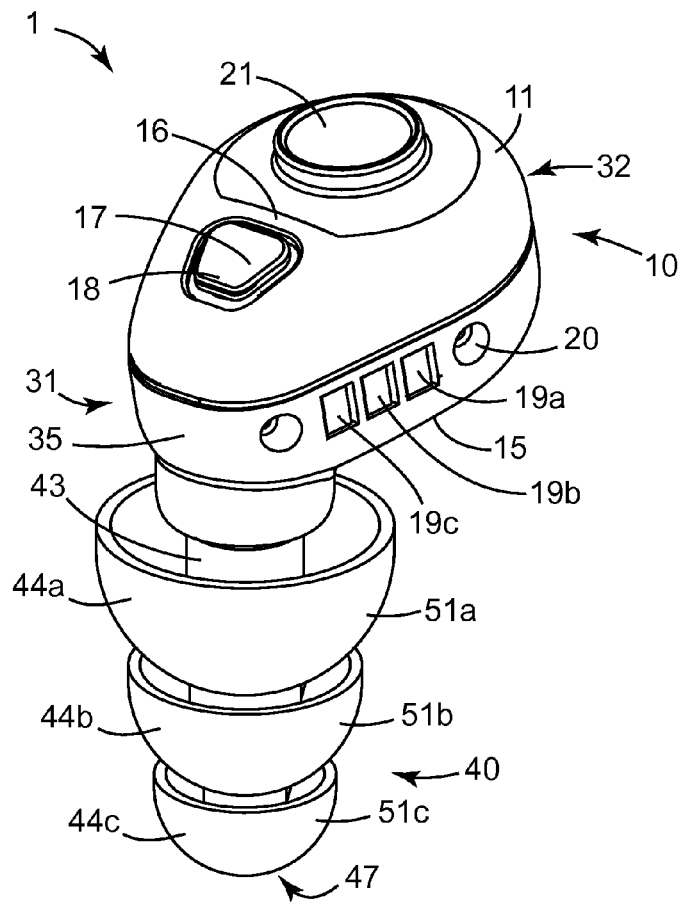
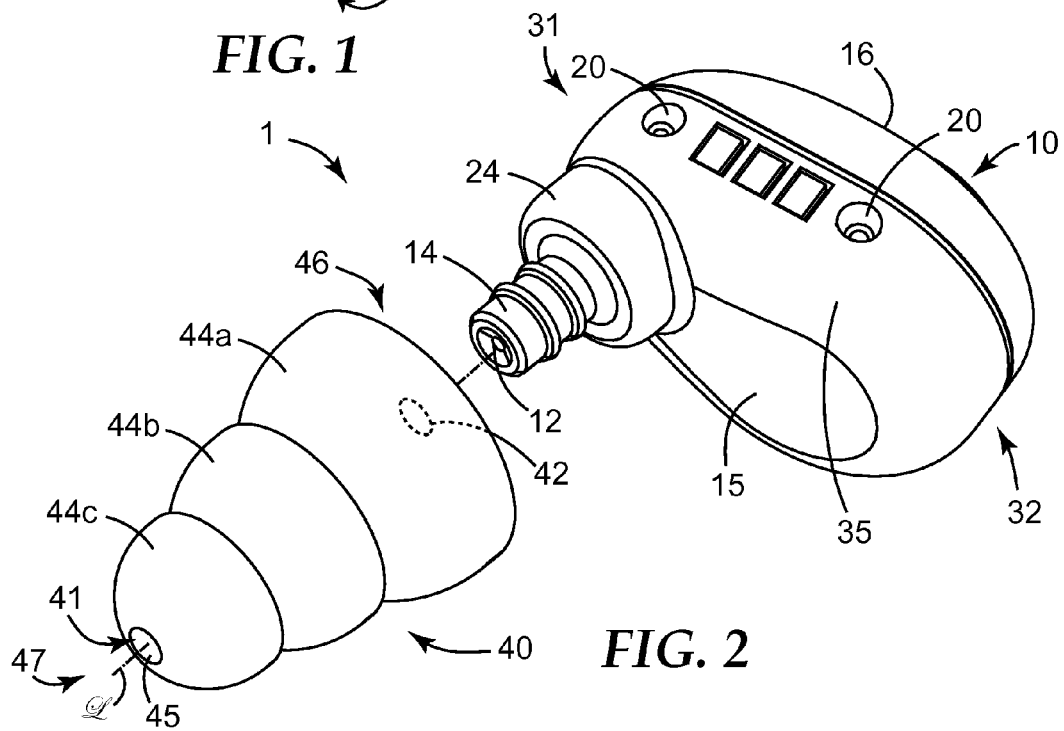

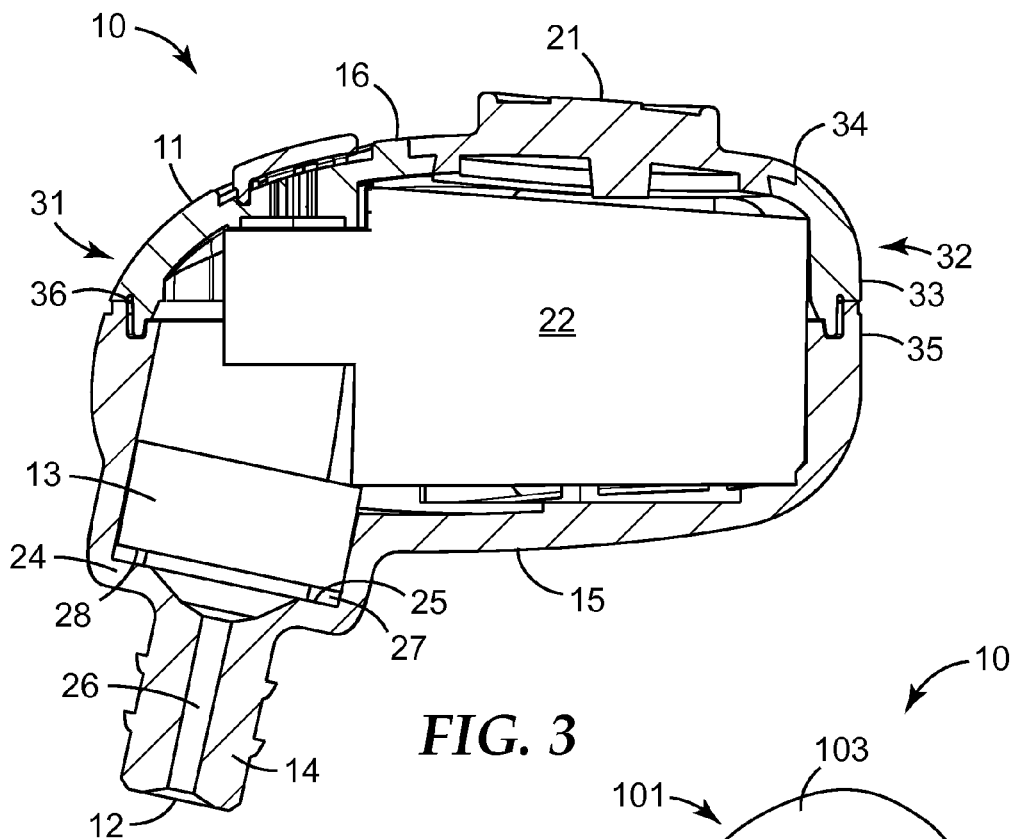
FIG. 3
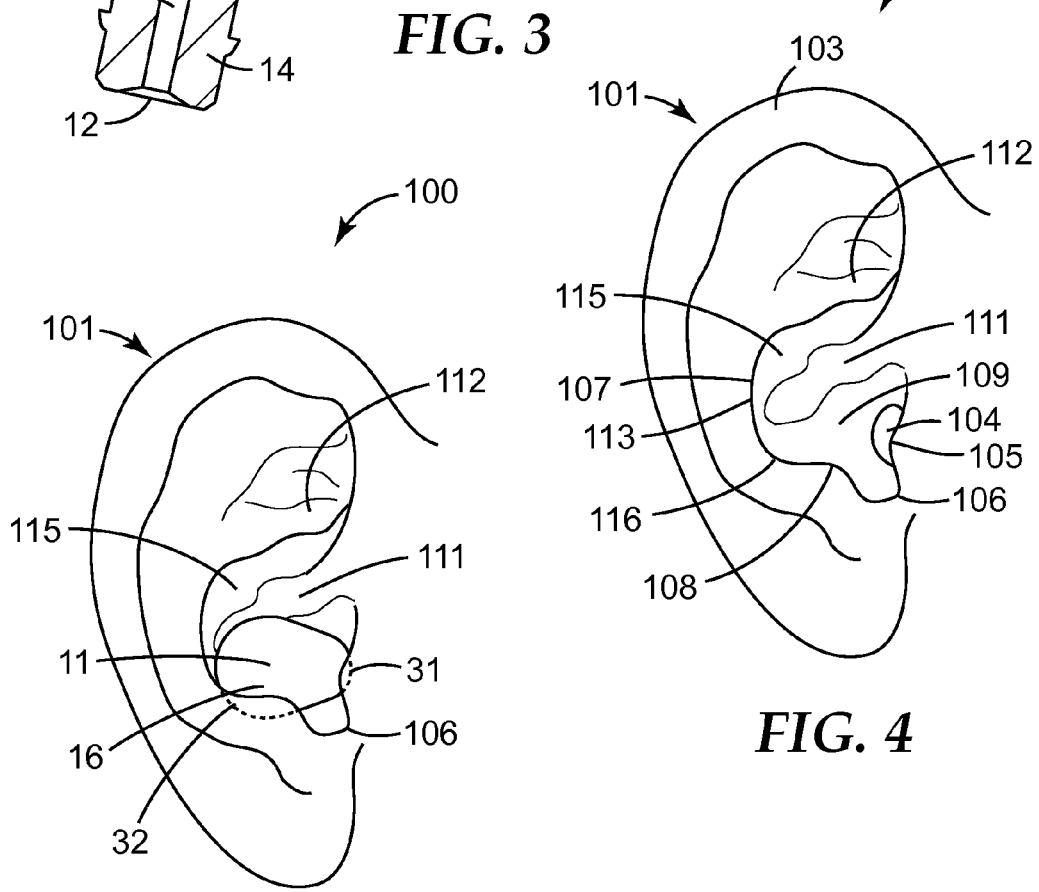
FIG. 4
FIG. 5

CONCHA-FIT ELECTRONIC HEARING PROTECTION DEVICE

BACKGROUND

Hearing protection devices are often used in, for example, industrial, military, and recreational applications.

SUMMARY

In broad summary, herein is disclosed an electronic hearing protection device configured to fit in the ear of a human user. The device comprises an earpiece body configured to fit in the concha of a user's ear and an eartip configured to fit into the ear canal of the user's ear, the eartip being detachably attached to the earpiece body and comprising a through-passage that is transmissive to airborne sound. When the device is fitted in the ear of a user, the eartip externally occludes the ear canal and the earpiece body internally occludes the eartip. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

BRIEF DESCRIPTION OF THE DRAWINGS

FIG. 1 is a perspective view of an exemplary device as disclosed herein.

FIG. 2 is a perspective exploded view of the device of FIG. 1.

FIG. 3 is a cross-sectional view of portions of an exemplary earpiece body of a device as disclosed herein.

FIG. 4 is a side view of a representative human ear.

FIG. 5 is a side view of an exemplary device as disclosed herein, as fitted into a human ear.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated.

For clarity of description of the device disclosed herein and its placement and functioning in a human ear, the following terminology will be adhered to. (All descriptions presented herein are with respect to a human right ear as viewed in the Figures and to a device fitted therein; it will be understood that corresponding descriptions apply to a human left ear and to a like device fitted therein.) As used herein, "inward" means toward the eardrum of the ear that the device is fitted in; "outward" means away from the eardrum of the ear that the device is fitted in. "Radially inward" and "radially outward" respectively mean inward and outward from an axis generally aligned with the long axis of an eartip (e.g. axis $\mathcal{L}$ as shown in FIG. 2) as disclosed herein. The terms clockwise and counterclockwise have their customary meaning. Terms such as upper, upward, top, above, and the like; and lower, downward, bottom, below, and the like; have their customary meaning with reference to an axis that runs generally up and down along the human ear (e.g., an earlobe is at the bottom of the human ear).

As used herein as a modifier to a property or attribute, the term "generally", unless otherwise specifically defined, means that the property or attribute would be readily recognizable by a person of ordinary skill but without requiring absolute precision or a perfect match. The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

DETAILED DESCRIPTION

As shown in exemplary embodiment in FIG. 1, disclosed herein is an electronic hearing protection device 1 that is suitable for fitting into the concha of a human ear. By an electronic hearing protection device is meant a device that substantially prevents ambient airborne sound from directly entering the ear canal, and that includes electronic components that receive ambient airborne sound, convert the sound to electronic signals, process the electronic signals, convert the processed electronic signals into processed sound, and then emit the processed sound through a speaker port, as described in detail later herein.

As shown in FIGS. 1 and 2, device 1 is comprised of two major components—eartip 40 and earpiece body 10. Earpiece body 10 is configured (i.e., shaped and sized) to fit into the concha of a human user's ear and is configured to receive sound, to perform appropriate signal processing, and to emit processed sound through a speaker port. Eartip 40 is configured (i.e., is shaped and sized and is comprised of a material of suitable softness) to fit into the ear canal of the user's ear (which terminology broadly denotes that at least a portion of eartip 40 fits into an outward portion of the ear canal and does not imply that the entirety of eartip 40 must be fitted into the ear canal). Eartip 40 is detachably attached to earpiece body 10 so that eartip 40 can be removed and cleaned or replaced if desired. Eartip 40 comprises a through-passage 41. By through-passage is meant that passage 41 extends through eartip 40 from outward end 46 to inward end 47 and allows the passage of airborne sound therethrough. In at least some embodiments, through-passage 41 is an internal through-passage, meaning that throughout all of its length, passage 41 is radially surrounded by material of eartip 40 (rather than being e.g. a groove or channel that is open to a radially outermost surface of eartip 40). Through-passage 41 (which may be at least generally aligned with a long axis of eartip 40, e.g. as depicted in FIG. 2) comprises a first, sound-receiving opening (e.g., opening 42 as depicted in FIG. 2) that is acoustically mated to a speaker port 12 of earpiece body 10, and a second, sound emitting opening 45 that faces toward the inner ear of the user, so that processed sound that is emitted from the speaker port can be transmitted through internal through-passage 41 and directed therefrom toward the inner ear of the user.

The fitting of at least a portion of eartip 40 into at least a portion of the ear canal externally occludes the ear canal. By externally occludes is meant that at least some radially outward surfaces (e.g., surfaces 51) of the eartip are in sufficient contact with portions of the walls of the ear canal to substantially prevent ambient airborne sound from traveling along the ear canal in a space otherwise existing between the eartip and the ear canal walls so as to reach the inner ear. However, eartip 40 alone may not completely occlude the ear canal, because through-passage 41 might allow ambient airborne sound to travel therethrough to reach the inner ear unless measures are taken to prevent this. Accordingly, the presence of earpiece body 10 (to which eartip 40 is attached) serves to internally occlude eartip 40. By internally occludes is meant that earpiece body 10 substantially prevents ambient airborne sound from entering first, sound-receiving opening 42 of eartip 40 while still allowing processed airborne sound to enter opening 42, as discussed in detail later herein.

The combination of the external occlusion of the ear canal achieved by eartip 40 and the internal occlusion of eartip 40 achieved by earpiece body 10 can provide excellent overall occlusion of the ear canal and can thus achieve a desired NRR (Noise Reduction Rating). Thus as disclosed herein, earpiece body 10 performs two separate functions, one electronic and one physical. That is, earpiece body 10 does not merely perform electronic processing (e.g., so-called level-dependent processing that allows high intensity sounds to be electronically reduced while low intensity sounds can be passed through or even amplified); it also provides a physical barrier that ensures that entry of ambient airborne sound into the through-passage of the eartip is sufficiently prevented so that a desirably high NRR can be achieved, as discussed in detail herein.

Eartip

An exemplary eartip 40 is shown in FIG. 1 and in isolated view in FIG. 2. By eartip is meant a body of which at least major portions thereof are resiliently compressible and/or deformable at least in a radially inward direction, so that when the eartip is inserted into an ear canal, at least some portions of the eartip are resiliently biased radially outward so that at least some radially outward surfaces of the eartip are held against portions of the walls of the ear canal so as to substantially or completely eliminate any air gap therebetween. Such an eartip thus substantially prevents ambient airborne sound from traveling down the ear canal in a space between the eartip and the ear canal walls (the body of the eartip itself will of course substantially prevent airborne sound from traveling through any space that the material of the eartip occupies). An eartip as defined herein thus specifically excludes any body (whether resiliently deformable/compressible or not) that comprises any kind of through-passage, channel, vent, notch, or the like (whether internal or external), that is configured to remain open so as to allow the transmission of airborne sound therethrough to reach the inner ear, when the body is fitted into an ear canal.

Eartip 40 comprises a long axis $\mathcal{L}$ that, when device 1 is fitted in the ear of a human user, will typically be at least generally aligned with a long axis of the portion of the ear canal into which the eartip is fitted. Eartip 40 comprises an outward end 46 and an inward end 47, end 46 being the end that is attached to earpiece body 10 and end 47 being the end that resides closest to the inner ear of the user. Eartip 40 may be comprised of any suitable material or materials, in any suitable geometric configuration. In some embodiments, eartip 40 may be comprised of a resiliently deformable and/or compressible organic polymeric material, e.g. a suitable molded plastic material. In embodiments of a first general type, the desired resilient compressibility of the eartip may be provided by properties of the organic polymeric material alone rather than by e.g. any particular geometric design. For example, in some embodiments eartip 40 might consist of a generally cylindrical and/or tapered main body, comprised e.g. of a resiliently compressible foam. In embodiments of a second general type, the desired resilient compressibility may be provided or enhanced by the geometric design of at least some components of the eartip. For example, as shown in exemplary manner in FIGS. 1 and 2, an eartip 40 may comprise a main body 43 comprising one or more radially-outward-protruding flanges 44 made of a resiliently deformable material. Insertion of such an eartip into an ear canal may result in such flanges being deformed (e.g., swept back toward outward end 46 of the eartip), with the desired resilient biasing of surfaces 51 of the flanges against the walls of the ear canal being thus achieved. In specific embodiments, one or more flanges 44 may be provided already in a swept-back (flared or bell-like) configuration even before being inserted into an ear canal (as shown in exemplary manner in FIGS. 1 and 2). In particular embodiments, such flanges may be at least generally semi-hemispherical in shape. It will be appreciated that in embodiments of this second general type, it may not be necessary that all, or even any, of the material of which eartip 40 is made must be significantly compressible, as long as at least certain components (e.g., flanges) of the eartip are resiliently deformable and are provided in geometric shapes that allow such deformation to provide the desired resilient biasing of surfaces of such components against the ear canal walls.

In some embodiments (whether eartip 40 comprises flanges or not), eartip 40 (e.g. main body 43 and any flanges that may be present) may consist of a single (e.g., molded) piece of organic polymeric material, e.g. a resiliently deformable and/or compressible material. In other embodiments, eartip 40 might comprise e.g. a main body that is not necessarily resilient and/or compressible, but radially outwards of which main body is mounted one or more resiliently deformable flanges, one or more annular layers of a resiliently compressible material, or the like. (It will be appreciated that in designs of the general type shown in FIGS. 1-3, it may be desirable that at least the outward portion of main body 43 of eartip 40 may be resiliently deformable, in order to facilitate e.g. the stretch-fitting of an outward opening (e.g., 42) of eartip 40 over protrusion 14 of earpiece body 10).

In some embodiments, eartip 40 may exhibit a tapered shape with inward end 47 (that faces toward the inner ear) being the narrow end, whether eartip 40 is in the form of a single piece, or whether such a tapered shape is provided stepwise by a plurality of flanges of different diameters. Although three flanges (44a, 44b, and 44c) each with ear canal wall-contacting surfaces (51a, 51b, and 51c, respectively) are shown in FIGS. 1 and 2, any number of flanges might be used. It will be appreciated that a wide variety of arrangements are possible and that the particular designs depicted in FIGS. 1 and 2 are merely exemplary embodiments. In various embodiments, a resiliently deformable and/or compressible portion of eartip 40 (or the entirety thereof), may be made of a material that exhibits a hardness of less than about 50, 45, 40, 35, 30, 25, or 20 on a Shore A scale. In particular embodiments, such an eartip or a portion thereof may be made of a material that exhibits a hardness of from about 30 to about 40 on a Shore A scale. Whatever the specific design of eartip 40, at least some portion of eartip 40 may conveniently be chosen to have a radial diameter that (when the components of eartip 40 are in an undeformed and/or uncompressed state) is at least somewhat larger than the average diameter of the outer ear canal of an adult human, in order to provide that insertion of eartip 40 into the ear canal will achieve the desired resilient biasing of surfaces of the eartip against the walls of the ear canal.

Eartip 40 can have any other features as desired. If desired, the internal through-passage 41 of eartip 40 can comprise one or more level-dependent sound attenuating physical (i.e., non-electronic) features. Such a feature could be e.g. an orifice, restriction, or obstruction that provides a reduced cross-sectional area for passage of sound therethrough, when compared to the average diameter of passage 41. Or, such a feature could be e.g. a diaphragm, a porous screen, mesh, or filter (such components are often referred to as acoustic dampers), and the like, as will be familiar to the ordinary artisan. In other embodiments, no level-dependent sound attenuating physical feature or features is present in passage 41 of eartip 40 (or e.g. in device 1 in general). For example, in some embodiments passage 41 might be e.g. a hollow conduit with an average diameter (or equivalent diameter) that does not vary by more than e.g. plus or minus 20% along its length.

Earpiece Body

An exemplary earpiece body 10 is shown in FIG. 1 and in isolated view in FIG. 2. Earpiece body 10 comprises a housing 11 which may be comprised of e.g. a molded polymeric material. In some embodiments, housing 11 may be formed by the mating together of two major housing parts, e.g. inward and outward major housing parts, as shown e.g. in FIGS. 1-3. Housing 11 is hollow so as to at least partially define interior space 22 (shown in FIG. 3) which may contain any suitable electronic components, one or more internal batteries, and so on. It will be appreciated that since housing 11 serves to protect various electronic components, a resiliently deformable and/or compressible material as may be used for eartip 40, may not be suitable for housing 11. That is, in at least some embodiments, housing 11 may be comprised of a rigid material. In various embodiments, housing 11 may be comprised of an organic polymeric material (e.g., a thermoplastic injection-molding resin) with a hardness of at least about 70, 80, 90 or 100 on a Shore A scale.

In particular embodiments, earpiece body 10 (e.g., housing 11 thereof) may comprise an internal battery (not shown in any Figure), a microphone 17 for receiving ambient airborne sound and for converting the received sound to electronic signals, circuitry (also not shown) for processing the electronic signals, and a speaker 13 (visible in FIG. 3) for transducing the processed signals into airborne processed sound. The term circuitry broadly encompasses any suitable components that may be desired to be used, e.g. one or more digital signal processors, analog-digital and/or digital-analog converters, data storage units, inductors, capacitors, resistors, and so on, whether such components are discrete components (e.g. mounted on a circuit board) or are provided as part of an integrated circuit. In some embodiments, the circuitry for processing the electronic signals is capable of performing level-dependent signal processing. In some embodiments, earpiece body 10 may comprise one or more electrical connections (three such connections 19a, 19b, and 19c are shown in FIGS. 1 and 2) by which an internal battery of device 1 can be recharged, and/or to allow communication with an external appliance (e.g. for configuring or programming device 1). One or more physical alignment features (e.g., sockets or protrusions) 20 may be provided to aid in aligning earpiece body 10 with a recharging unit and/or an external appliance. One or more switches 21 (of any suitable type, e.g. a touch-sensitive switch) may be provided to perform any desired function (e.g., turning the device on and off, switching between settings, increasing or decreasing volume, attenuation/gain, or any other parameter, and so on). That is, the term switch is used broadly to encompass any mechanism by which a user can vary any electronic operating variable of device 1 between two or more settings, whether in discrete steps or in a continuous manner. If switch 21 is a touch-sensitive switch, it may be of any suitable type, operating by any suitable mechanism (e.g., it might be an electrically-operating switch such as a capacitive, resistive, or piezo switch; or, it might be a mechanical switch).

Speaker port 12 of earpiece body 10 may be conveniently provided in a location which allows a first, sound-receiving opening 42 of through-passage 41 of eartip 40 to be acoustically mated thereto. By "acoustically mated" is meant that speaker port 12 of earpiece body 10 and the first, sound-receiving opening of eartip 40 are directly fluidly connected with each other so that sound waves emitted from speaker port 12 are able to travel directly therefrom into opening 42. In an exemplary embodiment most easily seen in FIGS. 2 and 3, speaker port 12 may be provided at the terminal end of a protrusion 14 that extends inward (when earpiece body 10 is fitted into a user's ear) so that when outward end 46 of eartip 40 is attached to protrusion 14, speaker port 12 and opening 42 of eartip 40 are aligned with each other and are in close proximity to each other. (In many embodiments outward end 46 of eartip 40 may be pushed onto protrusion 14 e.g. to provide a secure connection via a compression fit, so that strictly speaking, the opening 42 of eartip 40 that receives the sound emitted from speaker port 12, may be located somewhat inward along through-passage 41 of eartip 40 rather than being at the outward terminus of through-passage 41). In some embodiments, protrusion 14 may be of the same composition and properties (e.g., made of the same material) as housing 11. In particular embodiments, protrusion 14 may be an integral portion of housing 11 (which condition encompasses the case that protrusion 14 is an integral portion of a major housing part, in the specific instance that housing 11 is formed by the mating together of two major housing parts).

Eartip 40 is attached to earpiece body 10 (e.g., outward end 46 of eartip is attached to protrusion 14 of earpiece body 10) in a detachable manner. By this is meant that a user can manually (i.e., with fingers alone, without the use of any special tools such as pliers, screwdrivers, pry bars, and so on) separate eartip 40 from earpiece body 10 so as to e.g. clean eartip 40, replace it with a new or cleaned eartip, and so on. In the particular embodiment shown in FIGS. 2 and 3, detachable attachment of eartip 40 to earpiece body 10 may be provided by a friction fit of an annular portion of main body 43 of eartip onto the radially outer surface of protrusion (post) 14. (Here and elsewhere, the term annular is used broadly and does not imply or require a strictly or even substantially circular geometry). Eartip 40 may be pushed onto post 14 so as to e.g. approach or contact speaker housing 24 (as illustrated e.g. in FIG. 1) As illustrated in FIGS. 2 and 3, one or more ridges or barbs may be provided on post 14 to enhance the friction fit and yet to allow the eartip to be manually removed when desired. It will be appreciated however that any suitable method of detachably attaching eartip 40 to earpiece body 10 can be used.

Any suitable transducer (e.g., speaker) may be used to receive processed signals from the circuitry of earpiece body 10 and to emit processed airborne sound therefrom. In some embodiments, such a speaker may be located in close proximity to speaker port 12 through which the processed sound is delivered to sound-receiving opening 42 of eartip 40. Another type of embodiment is shown in FIG. 3, which is a cross-sectional view of earpiece body 10. In designs of this type, speaker 13 may be located a short distance (e.g., a few mm) away from speaker port 12 toward interior space 22 of earpiece body 10. For example, speaker 13 may be provided within a speaker housing 24 of housing 11, which speaker housing may be shaped and sized to receive speaker 13 therein. As seen in FIG. 3, speaker 13 may be oriented so that airborne sound emitted therefrom travels down speaker housing conduit 26 of speaker housing 24 to reach speaker port 12. In some embodiments, the entirety of speaker housing conduit 26 is defined by surfaces that are integral to speaker housing 24, e.g., that are integral to housing 11. (In the exemplary embodiment depicted in FIG. 3, the surfaces of speaker housing conduit 26 are defined by surfaces that are integral to the inward major housing part of the two major housing parts that are assembled together to form housing 11). It will be apparent, of course, that these are exemplary designs and that, for example, a protrusion 14 might not necessarily be used; rather, a portion of main body 43 of eartip 40 might e.g. penetrate into housing 11 of earpiece body 10 and be detachably attached to a speaker port-containing component that resides within housing 11.

As mentioned earlier herein, earpiece body 10 serves not only to provide processed sound via its electronic circuitry; it also serves to internally occlude through-passage 41 of eartip 40 to substantially prevent ambient airborne sound from entering thereinto. To enhance this functioning, various measures can be taken.

A first general measure is that housing 11 of earpiece body 10 can be configured so as to minimize the entry of ambient airborne sound into interior space 22 of earpiece body 10. This may be done by e.g. minimizing the number and size of any through-openings in housing 11. In particular embodiments, device 1 can use a rechargeable battery, which eliminates the need for a battery door (with the term door being used broadly to encompass any kind of opening, cover, etc., hinged or otherwise) through which a replaceable battery could be removed. The ordinary artisan will appreciate that such a battery door, even when closed, can comprise e.g. slit leaks that might allow ambient airborne sound to enter interior space 22 of earpiece body 10. Thus in specific embodiments, housing 11 of earpiece body 10 of device 1 does not comprise any battery door. Beyond this, housing 11, if made e.g. of two major housing parts that are mated together (assembled) to form housing 11, may be configured so as to not be disassemblable by a user (e.g., to replace a battery) in ordinary use of device 1. That is, such major housing parts may be configured to fit together with very close tolerances (and/or to provide a circuitous path through junction 36 therebetween, as shown in exemplary embodiment in FIG. 3), and/or the junction between such major housing parts may comprise any suitable gaskets, sealants, adhesives, and the like, as can e.g. provide a tight seal therebetween. Such provisions can further minimize the entry of ambient airborne sound into interior space 22 of earpiece body 10.

Still further, for locations of housing 11 at which a through-opening might be necessary e.g. to accommodate a component such as e.g. an electrical connection, a switch, a microphone, and so on, such components may be mated to their respective through-openings so that they at least substantially occlude their respective openings (e.g., to form a tight seal). In similar manner as described with regard to the mating of major housing parts, any suitable gasket, sealant, adhesive, or the like, can be used in mounting any such component to a through-opening in housing 11. Such arrangements can further minimize the amount of ambient airborne sound that is able to penetrate into interior space 22 of earpiece body 10.

The collective effect of such arrangements in minimizing the number and/or magnitude of e.g. air leaks in housing 11 may be gauged by the determination of an Ingress Protection Rating for housing 11 and/or for any component thereof. Such a Rating can be determined in accordance with Publication 60529 (Classification of Degrees of Protection Provided by Enclosures) as specified in 2013 by the International Electrotechnical Commission. (It will be appreciated that for purposes of such testing, speaker port 12 of housing 11 can be sealed.) An Ingress Protection Rating (also known as an IP Code or International Protection Rating) provides two numerical parameters. The first parameter denotes the ability of an enclosure to resist the penetration of solid objects, and has a scale of 0-6, with e.g. 0 indicating no protection and 6 indicating protection from ingress of dust. The second parameter denotes the ability of an enclosure to resist the penetration of liquid, and has a scale of 0-7, with e.g. 0 indicating no protection and 7 indicating protection from ingress of water upon immersion in water to a depth of between 15 centimeters and 1 meter. In various embodiments, housing 11 of device 1 may exhibit an Ingress Protection Rating of at least IP56, IP57, or IP66. In specific embodiments, housing 11 may exhibit an Ingress Protection Rating of IP67. The ordinary artisan will appreciate that housings that appear to comprise e.g. one or more unoccluded through-passages (such as e.g. the housing shown in FIGS. 1 and 2 of U.S. Patent Application Publication 2011/0103605 to Killion) would not be expected to exhibit an Ingress Protection Rating of IP67.

In addition to the above-discussed measures, the wall thickness (as well as the stiffness and other mechanical properties) of housing 11 may also be chosen so that ambient airborne sound striking the exterior surfaces of housing 11 does not cause the walls of housing 11 to deform or vibrate in such manner as to unacceptably re-transmit ambient airborne sound into interior 22 of earpiece body 10.

Beyond the above arrangements, a second general measure can be taken to provide that, even if some ambient airborne sound is able to penetrate into interior space 22 of earpiece body 10, such ambient airborne sound may not be able to travel therefrom into through-passage 41 of eartip 40. Specifically, speaker 13 can be arranged so that the body of speaker 13 acts as a physical barrier to minimize the entry of ambient airborne sound into through-passage 41 of eartip 40. For example, speaker 13 can be positioned so that a movable component (e.g., a diaphragm) thereof can emit processed sound into speaker housing conduit 26, while a non-movable surface of speaker 13 (e.g., a mating surface 28 that may e.g. annularly surround the movable component) can be mated against a seating surface 25 of speaker housing 24 (as shown in FIG. 3). This mating can substantially prevent any ambient (unprocessed) airborne sound that may be present within interior 22 of earpiece body 10, from entering speaker housing conduit 26 and thus being able to enter through-passage 41 of the eartip. This mating can be direct, or indirect, as desired. In some embodiments, indirect mating can be achieved by providing a sealing layer 27 (e.g., of a compliant material) between mating surface 28 of speaker 13 and seating surface 25 of speaker housing 24 (as shown in FIG. 3). Such a sealing layer may be provided in the form of a (preformed) gasket, o-ring, or the like. Or, such a sealing layer may be provided by e.g. a liquid or semi-solid material (e.g., a caulk). In particular embodiments, an adhesive may be used (whether e.g. a flowable or liquid adhesive, a pressure-sensitive adhesive, and so on) which may perform the dual functions of helping secure speaker 13 in place in speaker housing 24, and also of providing sealing layer 27. Such arrangements, however achieved, can provide that if any ambient airborne sound does penetrate into interior 22 of earpiece body 10, the ambient airborne sound may be substantially prevented from entering through-passage 41 of eartip 40.

It is noted that the mating of a mating surface of a speaker to a seating surface of a speaker housing as disclosed herein (whether done directly or indirectly), is by definition different from an arrangement in which a so-called "sound tube" is used to provide a path from a speaker to an eartip through-passage, such a sound tube being an elongate member that is not integrally formed with the housing of an earpiece body (i.e., that is not integrally formed with any major housing part thereof, in the case that a housing is formed by the mating together of two major housing parts). Arrangements using a sound tube can be found e.g. in FIGS. 1 and 2 of U.S. Patent Application Publication 2011/0103605 to Killion)

By the arrangements disclosed herein, the ability of ambient airborne sound to penetrate through housing 11 into the interior space 22 of earpiece body 10, and the ability of any such ambient airborne sound that has managed to penetrate into interior 22 to proceed therefrom into through-passage 41 of eartip 40, can be minimized. (That is, the arrangements disclosed herein can provide that substantially the only airborne sound that is able to enter sound-receiving opening 42 of eartip 40, is processed sound that is emitted by speaker 13.) In other words, these arrangements can allow earpiece body 10 to internally occlude through-passage 41 of eartip 40. This, coupled with the ability of eartip 40 to externally occlude the ear canal, can provide significant advantages as discussed earlier herein. In various embodiments, the external occluding of the ear canal by eartip 40 and the internal occluding of eartip 40 by earpiece body 10 can combine to provide a Noise Reduction Rating (NRR) of at least about 18, 20, 22, 24, 26, 28, 30, or 33 dB. Such a Noise Reduction Rating can be measured e.g. by the use human subject testing in accordance with ANSI S3.19-1974.

In the discussions herein, various devices, components and arrangements have been characterized as e.g. "substantially preventing" the passing of airborne sound waves. It will be understood that such terminology does not require that such a device, component or arrangement necessarily provide an absolute barrier to airborne sound. Rather, the only requirement signified by this terminology is that all such components and arrangements collectively provide sufficient barrier properties to airborne sound that device 1, comprising eartip 40 and earpiece body 10 as disclosed herein, is capable of functioning as disclosed herein.

Ear Physiology and Fitting of Device in Ear

The physiology and features of a human ear will be briefly summarized so that the fitting of the present device into the ear of a user can be described in precise detail. With reference to FIG. 4, the external human ear 100 includes a broad structure 101 called the pinna. Pinna 101 includes a prominent exterior curved rim 103 called the helix, that originates in an upper base region 111 called the helix crus, and that extends therefrom in a counterclockwise direction along the radially outer edge of the pinna. Radially inward from the helix 103 is another curved prominence 107 called the antihelix, which extends from an upper base region 112 called the antihelix crura, in a generally counterclockwise direction so as to partially circumferentially surround a somewhat bowl-shaped depression 106 known as the concha. Concha 106 is at least partially divided by the helix crus 111 into a lower part 109 called the cavum concha, and an upper part 115 called the cimba concha. The inwardmost regions of concha 106 lead to the ear canal 104, which is a somewhat circular or oval (in cross-section) passage that leads to the eardrum and the inner ear.

The antihelix 107 exhibits a radially inward-facing rim 113 which, along at least some or most of its length, may protrude slightly radially inward so as to provide a lip or flange that slightly overhangs the radially outward edge of concha 106. The lowermost portion of the antihelix 107 (e.g., portion 116 as shown in FIG. 4) becomes the antitragus 108, which is a prominence that extends radially inward over the edge of the cavum concha (and which typically exhibits a more pronounced radially-inwardly-extending lip than does antihelix 107). Across the lower portion of the cavum concha from the antitragus is another radially-inward-extending prominence 105 called the tragus, which (in similar manner to the antitragus), typically exhibits a more pronounced lip than does the antihelix, and which may often slightly outwardly cover a portion of the ear canal 104.

Device 1 as disclosed herein is configured (sized and shaped) so that device 1 can be securely and comfortably retained in place in the ear of a user without requiring device 1 to be custom-shaped to fit in the ear of that specific user. Device 1 (and earpiece body 10 and eartip 40 thereof) is thus by definition not a custom-made device (e.g., a device of which any portion of any component is made according to a mold or 3-D image of the ear of a particular user). In at least some embodiments device 1 is configured so that it can fit in the right ear of a user and can also fit in the left ear of the user. In such embodiments it is not necessary to provide differently-configured (e.g., shaped) devices to be used in the right and left ears of a user; rather, a pair of identically shaped devices can be supplied. This may done e.g. by providing earpiece body 10 in a shape that has sufficient bilateral symmetry (i.e., when viewed along a direction generally aligned with the long axis of eartip 40) to fit comfortably in a right ear or in a left ear, as desired. It is noted however that this desire for the overall shape of housing 11 to have sufficient bilateral symmetry to function in this manner, does not require that the placement of various features (e.g., microphone, switch, electrical contacts) of earpiece body 10 must exhibit bilateral symmetry. Nor does it preclude the presence of small, local asymmetries in the shape of housing 11, as long as sufficient bilateral symmetry of the overall shape of housing 11 is maintained.

The degree of overall bilateral symmetry of the shape of housing 11 may be gauged by taking the projected area of housing 11 on a plane that is substantially perpendicular to the long axis of eartip 40 (notwithstanding any slight offset angle that may be present, as discussed later herein), and identifying an axis of symmetry that runs at least generally along a long axis of the projected area and that divides the projected area into two (e.g. roughly equal) partial-areas. One of the partial-areas can then be rotated around the axis of symmetry onto the other partial-area (i.e., as if folding the projected area along the axis of symmetry to bring one partial-area over onto the other partial-area). The percentage of their areas that the two partial-areas share in common can be measured and represents the degree of bilateral symmetry that exists. By a housing having an at least generally bilaterally symmetrical shape is meant that two partial-areas generated and measured in this manner share at least 70% of their area in common. In various embodiments, housing 11 may comprise a bilateral symmetry of at least about 80, 90, 95, or 98%.

In at least some embodiments, housing 11 of earpiece body 10 may be provided in a generally oval shape (when viewed along the long axis of eartip 40). The terminology of generally oval includes ovals, ellipses, rectangles with one or more rounded corners, teardrop shapes, and so on. In the specific embodiment illustrated in FIGS. 1-3 and 5, housing 11 is of generally oval shape with end 31 (to which end eartip 40 is detachably attached) being somewhat narrower than opposite end 32 (thus housing 11 is somewhat teardrop-shaped, with a tapered end 31 and a blunt end 32, in this embodiment).

Shapes of these general types may allows one or more surfaces of housing 11 to reside closely adjacent to (and in some embodiments to contact) a surface of an ear component that defines at least a portion of the radially outer perimeter of concha 106. Such ear components may include e.g. any or all of the tragus 105, the antitragus 108, and portions of the radially inward-facing rim 113 of the antihelix 107. Such arrangements can serve (e.g. in combination with the fitting of eartip 40 in ear canal 104) to retain device 1 securely and yet comfortably in the concha 106 of a human ear. This is illustrated in exemplary manner in FIG. 5, which shows an exemplary earpiece body 10 (with eartip 40 and ear canal 104 omitted from this view for ease of presentation) seated in the right ear of a human user.

The dimensions and shape of housing 11 of earpiece body 10 are thus configured so that housing 11 can be fitted into in the concha 106 (in specific embodiments, into the cavum concha 109) of a human ear. For example, inward surface 15 of housing 11 may be shaped so that when device 1 is fitted in the ear, some or most of the area of inward surface 15 of housing 11 may be in contact with (skin) surfaces that define the inward limits of concha 106. And, as mentioned above, one or more contact surfaces of housing 11 (e.g., surface 33 as shown in FIG. 3) can be provided (whether spaced apart, or extending continuously) around at least a portion of the perimeter of housing 11, which contact surface or surfaces are configured so that when device 1 is fitted in the ear of a user, at least one contact surface is in contact with a (skin) surface of an ear component that defines at least a portion of the radially outer perimeter of concha 106 (e.g., of cavum concha 109).

In some embodiments, housing 11 can be sized and shaped so that at least one generally outward-facing contact surface (e.g. surface 34 as shown in FIG. 3) of housing 11 is able to fit at least partially inwardly underneath (and in some embodiments, to contact) an inwardly-facing surface of a radially-inwardly-protruding edge (e.g., lip) of an ear component that defines a portion of the radially outer perimeter of the concha. Thus, in some embodiments, housing 11 of earpiece body 10 may comprise various contact surfaces (whether of the general orientation exemplified by surface 33, or the general orientation exemplified by surface 34, both as shown in FIG. 3) that are respectively configured to reside in radially-inward proximity, and/or in inward proximity, to a radially inward-facing surface (e.g., a radially-inward-protruding lip) of the tragus 105, of the antitragus 108, and/or of a portion 116 of the antihelix that is proximate the antitragus. (In this context, by a portion of the antihelix that is proximate the antitragus means a portion that is within about 25 mm of the radially-inwardmost-projecting part of the antitragus, measured in a clockwise direction around the antihelix.) One such configuration is shown in exemplary illustration in FIG. 5, in which a contact surface of blunt end 32 of housing 11 inwardly underlies, and may be in contact with, a portion of a lip of antitragus 108; and, a contact surface of tapered end 31 of housing 11 inwardly underlies, and may be in contact with, a portion of a lip of tragus 105. It is emphasized that in various instances (e.g., depending on the specific shape of the components of a particular user's ear), any individual contact surface or portion thereof, may or may not necessarily contact the (skin) surface of an ear component that defines at least a portion of the radially outer perimeter of the concha of that user's ear.

Thus in broad summary, housing 11 may be configured so that device 1 may be held in position in a human ear by way of at least one contact surface of housing 11 of earpiece body 10 of device 1 being adjacent to (e.g., in contact with) a skin surface that defines at least a portion of the radially outer perimeter of concha 106, in combination with the fitting of eartip 40 into ear canal 104. Such arrangements may be distinguished from arrangements in which a device is fully supported by the fitting of an eartip of the device into the ear canal, with no contribution from the placement of any contact surface of a housing adjacent to or in contact with any portion of the radially outer perimeter of the concha. In further embodiments, housing 11 may be configured so that device 1 may be held in position in a human ear at least in part by way of two or more contact surfaces of housing 11 (e.g., at different locations along the radially outer perimeter of housing 11) of earpiece body 10 being adjacent to (e.g., in contact with) respective skin surfaces that define at least a portion of the radially outer perimeter of concha 106. In various embodiments, when device 1 is fitted into the ear of a user, two such areas of contact between contact surfaces of housing 11 and surfaces of ear components defining portions of the radially outer perimeter of concha 106, may be spaced around the perimeter of housing 11 with a circumferential separation of at least 120, 140, or 160 degrees (in either a clockwise or a counterclockwise direction). Such an arrangement is shown in exemplary embodiment FIG. 5, with two such areas of contact (with a portion of the tragus, and with a portion of the antitragus, respectively) having a circumferential separation judged to be in the range of about 130 degrees.

While in some embodiments the fitting of eartip 40 into ear canal 104 may augment the above effects in securely fitting device 1 into a human ear, the providing of at least one contact surface (and particularly, two or more such surfaces) around the perimeter of housing 11 may allow for less aggressive fitting of eartip 40 into the ear canal (that is, eartip 40 may not need to be fitted as deep into the ear canal), thus providing increased comfort for the user while allowing device 1 to still be securely held in place. That is, in such embodiments eartip 40 may only need to be fitted into the ear canal to an extent sufficient to provide the aforementioned external occlusion rather than to serve as the primary mechanism for securing device 1 in the ear. Thus in some embodiments device 1 may be held in place in the ear partially, substantially or completely by way of a compression fit of housing 11 of earpiece body 10 of device 1, between portions of components defining the radially outer perimeter of the concha, e.g. between any combination of a tragus, an antitragus, and/or a portion of an antihelix that is proximate the antitragus, of a user's ear.

In some embodiments, the inward-outward dimension of earpiece body 10 (i.e., the distance between inward surface 15 and outward surface 16 or a component (e.g. a microphone or switch) protruding outwardly therefrom) may be kept to a minimum so that no portion of earpiece body 10 extends outward beyond an imaginary plane that coincides with the outwardmost limit of the antihelix. This may provide that device 1 may be comfortable to wear even when a user is sleeping (e.g., so that device 1 does not protrude so far outward that positioning the user's head and ear in contact with a pillow might cause device 1 to exert an uncomfortable force on the user's ear). In at least some embodiments, when device 1 is fitted into a user's ear, all parts of earpiece body 10 may be generally, substantially, or completely, located within the cavum concha. In particular, in some embodiments earpiece body 10 will not comprise any protrusion that, when device 1 is fitted into a user's ear, extends upward into the cimba concha (e.g., in the manner of an arcuate protrusion that follows, and/or rests radially inward of, the rim of the cimba concha).

In some embodiments, an offset angle may be present between long axis $\mathcal{L}$ of eartip 40 and housing 11 of earpiece body 10. Such an offset angle may provide enhanced comfort of device 1 when fitted into a users ear. For ease of description, such an offset angle may be characterized with reference to an axis that is normal to the major plane of inward surface 15 of housing 11, at a position located radially centrally on housing 11 (e.g., in the specific location denoted by reference number 15 in FIG. 3). Thus, the exemplary design shown in FIGS. 1-3 provides an offset angle between long axis $\mathcal{L}$ of eartip 40, and such a normal axis, of approximately 12 degrees negative (i.e., long axis $\mathcal{L}$ is angled away from the radially central location of housing 11). In various embodiments, an offset angle between the long axis of eartip 40, and earpiece body 10, may be at least about negative 6, 8, or 10 degrees. In further embodiments, such an offset angle may be at most about negative 18, 16, or 14 degrees. In many embodiments, the orientation of long axis $\mathcal{L}$ of eartip 40 may be dictated by the orientation of a mounting structure (e.g., protrusion 14) of housing 11 to which eartip 40 is mounted. Thus, in many embodiments, such an offset angle may established e.g. by the angle at which protrusion 14 extends away from housing 11 of earpiece body 10, as is the case in the exemplary embodiment best seen in FIG. 3.

The above discussions are to be interpreted in view of the fact there exists some variation in the shape of human ears. Thus, the descriptions provided herein of fitting device 1 into a human ear, e.g. a concha, will be understood as applying to adults with ear geometries and features that would be considered by an audiologist as being representative of the average adult population of humans. It is noted that device 1 (specifically, earpiece body 10 and/or eartip 40 thereof) may be provided in multiple sizes, with, for any device 1, the above descriptions being valid for at least the particular human population for which that size device 1 is configured. In specific embodiments, the fitting of device 1 into a concha as described herein may be evaluated with respect to the fitting of device 1 into an artificial ear (i.e., a molded plastic artificial pinna) suitable for use in the test methods outlined in ANSI S12.42 (Methods for the Measurement of Insertion Loss of Hearing Protection Devices in Continuous or Impulsive Noise Using Microphone-in-Real-Ear or Acoustic Test Fixture Procedures) as specified in 2010. A specific example of such artificial ears are those available under the trade designation KB0065 (right) and KB0066 (left) (normal—large) from G.R.A.S. Sound & Vibration A/S (Holte, Denmark) for use with the G.R.A.S. 45BC KEMAR Head and Torso with Mouth Simulator. Thus, in specific embodiments, housing 11 of device 1 is configured to have at least one contact surface that is configured to contact a "skin" surface that defines at least a portion of the radially outer perimeter of a concha, of an artificial ear that meets the requirements for use with the ANSI S12.42 test method.

Other arrangements may be provided to assist in the comfortable functioning of device 1. For example, one or more switches 21, if present, may be located on an outward surface 16 of housing 11, in a location that is displaced radially off-axis (e.g., by at least 2, 4, 6, or 8 mm) from the long axis of eartip 40. This can provide that, e.g. if a switch 21 is activated by physical pressure, it is not located in alignment with the ear canal such that pushing switch 21 inward would tend to force eartip 40 deeper into the canal. Rather, such off-axis placement can provide that any force applied to switch 21 may be dissipated over some or all of the contact area between inward surface 15 of housing 11 and the skin surfaces of the user's concha. Moreover, such an arrangement can allow microphone 17 to be at least generally aligned with (e.g., within at most 4, 3, 2 or 1 mm of) the long axis of eartip 40. This can advantageously place microphone 17 in alignment with the ear canal, so that microphone 17 is well-positioned to receive sound that has been gathered and reflected by the various surfaces of the pinna. Moreover, placement of microphone 17 relatively deep inward within concha 106 may shield microphone 17 from wind noise (a windscreen 18, as shown in exemplary manner in FIG. 1, may also be used if desired). Moreover, the use of contoured surfaces on the generally outward-facing side 16 of housing 11, and the absence of any components (such as e.g. switches, graspable members to facilitate removal of the device from a user's ear, and so on) that protrude outward more than e.g. a mm or two beyond the adjacent outward surface 16 of housing 11, may reduce any turbulence that might be caused by impingement of wind onto exposed sharp-edged and/or protruding surfaces of earpiece body 10, and may further minimize the effect of any wind noise on microphone 17. Thus, in specific embodiments, the junction between surface 35 of the sidewalls of housing 11 and outward surface 16 of housing 11, may comprise a radius of curvature that is at least about 1.5, 2.0, 3.0, or 4.0 mm at all locations around the outer perimeter of housing 11.

If desired, device 1 may be provided with the ability to receive data from external devices (e.g., smart phones and the like) e.g. via physical connections, by wireless communication, and so on. In some embodiments, such data may be processed and converted to airborne sound (emitted by speaker 13) so that device 1 receive e.g. wireless voice transmissions and can then convey them to the user as airborne sound. In some embodiments two devices 1 may be configured to communicate with each other, so that e.g. a change (e.g., increase or decrease in volume, gain, and so on) applied to one device can be automatically communicated to, and applied by, the other device. In some embodiments two devices 1 may be connected to each other by way of a tether, which can be used in any customary manner.

Charging Unit and Kits

Device 1 may conveniently comprise one or more internal electric power sources, e.g. batteries. In some embodiments, such a battery or batteries may be a one-use battery that can be properly disposed and replaced. In other embodiments, such a battery or batteries may be rechargeable, and may be charged or recharged by way of an external charging unit that is electrically connected to device 1 (e.g. by way of any or all of conductive contacts 19a, 19b, and 19c). In some embodiments, such charging might be performed by way of inductive charging, thus the providing of conductive contacts might not be necessary.

In some embodiments, such a charging unit may be portable (e.g., pocket-sized), and may itself be powered by batteries (which may have sufficient capacity to provide e.g. 5, 10, 20, or more chargings of e.g. one or two devices 1). A charging unit of this general type may also serve as a portable storage and carrying unit for device 1 (such a unit may be designed to hold two such devices 1). Thus, in some embodiments, one, two, or more devices 1 may be supplied as a kit in combination with a charging unit. In further embodiments, one or more (e.g., two) earpiece bodies 10 may be supplied as a kit in combination with multiple (e.g., two, four, six, or more) eartips 40, which eartips may be of different sizes.

LIST OF EXEMPLARY EMBODIMENTS

Embodiment 1 is an electronic hearing protection device configured to fit in the ear of a human user, comprising: an earpiece body configured to fit in the concha of a user's ear and configured to receive sound, to process the sound, and to emit processed sound through a speaker port; and, an eartip configured to fit into the ear canal of the user's ear, the eartip being detachably attached to the earpiece body and comprising a through-passage with a first, sound-receiving opening that is acoustically mated to the speaker port of the earpiece body and with a second, sound-emitting opening that faces toward the inner ear of the user, wherein the device is configured so that when the device is fitted in the ear of a user, the eartip externally occludes the ear canal and the earpiece body internally occludes the eartip, and wherein the earpiece body comprises a housing that exhibits an at least generally bilaterally symmetrical shape when viewed along a long axis of the eartip and that comprises at least one contact surface that is configured so that when the device is fitted in the ear of a user, the at least one contact surface of the housing contacts a skin surface of an ear component that defines at least a portion of a radially outer perimeter of the concha of the user's ear.

Embodiment 2 is the device of embodiment 1 wherein the at least one contact surface of the housing is configured so that when the device is fitted in the ear of a user, the at least one contact surface of the housing contacts at least one of a skin surface of a tragus, an antitragus, and a portion of an antihelix that is proximate the antitragus, of the user's ear. Embodiment 3 is the device of any of embodiments 1-2 wherein the housing comprises at least first and second contact surfaces that are configured so that when the device is fitted in the ear of a user, the first contact surface contacts a first portion of a first skin surface of a first ear component that defines a first portion of the radially outer perimeter of the concha of the user's ear, and a second contact surface contacts a second portion of a second skin surface of a second ear component that defines a second portion of the radially outer perimeter of a concha of the user's ear, with the areas of contact between the first and second contact surfaces of the housing and the skin surfaces with which they are respectively in contact with, being spaced around the perimeter of the housing with a circumferential separation of at least about 120 degrees. Embodiment 4 is the device of any of embodiments 1-3 wherein the housing is configured so that when the device is fitted into the user's ear, the device is held in the ear at least in part by a compression fit of the housing of the earpiece body of the device, with at least any two of a tragus, an antitragus, and a portion of an antihelix that is proximate the antitragus, of the user's ear. Embodiment 5 is the device of any of embodiments 1-4 wherein the earpiece body is configured to fit at least substantially in the cavum concha of a user's ear. Embodiment 6 is the device of any of embodiments 1-5 wherein no part of the earpiece body extends into the cimba concha of the user's ear. Embodiment 7 is the device of any of embodiments 1-6 wherein no part of the earpiece body extends outward of the cavum concha of the user's ear.

Embodiment 8 is the device of any of embodiments 1-7 wherein the device provides a Noise Reduction Rating of at least about 18 dB. Embodiment 9 is the device of any of embodiments 1-8 wherein the housing is configured to at least substantially prevent the entry of ambient airborne sound into the interior thereof, and wherein the housing exhibits an Ingress Protection Rating of IP67. Embodiment 10 is the device of any of embodiments 1-9 wherein the housing does not comprise any unoccluded through-openings. Embodiment 11 is the device of any of embodiments 1-10 wherein the device contains an internal, rechargeable, non-removable battery that is located within the housing, and wherein the housing does not comprise a battery door. Embodiment 12 is the device of any of embodiments 1-11 wherein the earpiece body contains a speaker with a mating surface that is mated against a seating surface of a speaker housing of the housing of the earpiece body so as to at least substantially prevent any ambient airborne sound that may be in the interior of the housing, from passing through the speaker port of the housing. Embodiment 13 is the device of embodiment 12 wherein the mating surface of the speaker is indirectly mated against the seating surface of the speaker housing; and, wherein the speaker housing is integral with at least a major housing part of the housing of the earpiece body and wherein the speaker housing comprises a speaker housing conduit that is entirely defined by surfaces that are integral with the speaker housing; and, wherein the speaker housing conduit receives airborne processed sound from the speaker and allows the airborne processed sound to pass therethrough to reach the speaker port.

Embodiment 14 is the device of any of embodiments 1-13 wherein the housing of the earpiece body comprises one or more electrical connections by which an internal, rechargeable, non-removable battery that is located within the housing can be charged. Embodiment 15 is the device of any of embodiments 1-14 wherein the through-passage of the eartip is an internal through-passage that is at least generally aligned with a long axis of the eartip. Embodiment 16 is the device of embodiment 15 wherein the internal through-passage of the eartip does not comprise any level-dependent sound attenuating physical feature. Embodiment 17 is the device of any of embodiments 1-16 wherein the eartip comprises a main body and further comprises at least one resiliently deformable flange that extends radially outward therefrom. Embodiment 18 is the device of embodiment 17 wherein the eartip comprises a multiplicity of radially outwardly extending resiliently deformable flanges of different diameters, which flanges are spaced along a long axis of the eartip so that the eartip exhibits an overall tapered shape with a large-diameter end of the tapered eartip being proximate the earpiece body. Embodiment 19 is the device of any of embodiments 1-18 wherein the eartip is a single piece of resiliently compressible organic polymeric material with a hardness of less than about 40 on a Shore A scale. Embodiment 20 is the device of embodiments 1-19 wherein the eartip is a single piece of resiliently compressible organic polymeric foam material.

Embodiment 21 is the device of embodiments 1-20 wherein the housing is comprised of a rigid molded polymeric material with a hardness of greater than about 70 on a Shore A scale. Embodiment 22 is the device of embodiments 1-21 wherein the detachable attachment of the eartip to the earpiece body is provided by a friction fit of an annular portion of a main body of the eartip onto a radially outward surface of a protrusion of the earpiece body, an inward end of which protrusion comprises the speaker port of the earpiece body. Embodiment 23 is the device of embodiments 1-22 wherein the earpiece body comprises a microphone for receiving ambient airborne sound and for converting the ambient airborne sound into electronic signals, circuitry for processing the electronic signals, and a speaker for emitting the processed electronic signals as processed sound. Embodiment 24 is the device of embodiment 23 wherein the circuitry for processing the electronic signals is configured to perform level-dependent signal processing. Embodiment 25 is the device of any of embodiments 23-24 wherein the microphone is provided on an outward face of the housing of the earpiece body, in a location that is aligned radially on-axis with a long axis of the eartip within a distance of about 2 mm. Embodiment 26 is the device of any of embodiments 23-25 comprising a touch-sensitive switch located on an outward face of the housing of the earpiece body, in a location that is displaced radially off-axis from a long axis of the eartip a distance of at least about 4 mm.

Embodiment 27 is a kit comprising at least two earpiece bodies of any of embodiments 1-26 in combination with at least four eartips of any of embodiments 1-26, at least some of the eartips being of different sizes from each other. Embodiment 28 is the kit comprising at least one device of any of embodiments 1-26, in combination with a charging unit configured to charge at least one internal battery of the earpiece body of the device. Embodiment 29 is the kit of embodiment 28, wherein the charging unit is a portable charging unit that comprises at least one internal battery and that does not require an external power source.

Embodiment 30 is an electronic hearing protection device configured to fit in the ear of a human user, comprising: an earpiece body configured to fit in the concha of a user's ear and configured to receive sound, to process the sound, and to emit processed sound through a speaker port; and, an eartip configured to fit into the ear canal of the user's ear, the eartip being detachably attached to the earpiece body and comprising a through-passage with a first, sound-receiving opening that is acoustically mated to the speaker port of the earpiece body and with a second, sound-emitting opening that faces toward the inner ear of the user, wherein the device is configured so that when the device is fitted in the ear of a user, the eartip externally occludes the ear canal and the earpiece body internally occludes the eartip, wherein the device provides a Noise Reduction Rating of at least about 18 dB and wherein the housing is configured to at least substantially prevent the entry of ambient airborne sound into the interior thereof and exhibits an Ingress Protection Rating of IP67. Embodiment 31 is the device of device of embodiment 30 wherein the housing does not comprise any unoccluded through-openings. Embodiment 32 is the device of any of embodiments 30-31 wherein the device contains an internal, rechargeable, non-removable battery that is located within the housing, and wherein the housing does not comprise a battery door. Embodiment 33 is the device of any of embodiments 30-32 wherein the earpiece body contains a speaker with a mating surface that is mated against a seating surface of a speaker housing of the housing of the earpiece body so as to at least substantially prevent any ambient airborne sound that may be in the interior of the housing, from passing through the speaker port of the housing. Embodiment 34 is the device of embodiment 33 wherein the mating surface of the speaker is indirectly mated against the seating surface of the speaker housing; and, wherein the speaker housing is integral with at least a major housing part of the housing of the earpiece body and wherein the speaker housing comprises a speaker housing conduit that is entirely defined by surfaces that are integral with the speaker housing; and, wherein the speaker housing conduit receives airborne processed sound from the speaker and allows the airborne processed sound to pass therethrough to reach the speaker port.

It will be apparent to those skilled in the art that the specific exemplary elements, structures, features, details, configurations, etc., that are disclosed herein can be modified and/or combined in numerous embodiments. (In particular, any of the elements that are positively recited in this specification as alternatives, may be explicitly included in the claims or excluded from the claims, in any combination as desired.) All such variations and combinations are contemplated by the inventor as being within the bounds of the conceived invention not merely those representative designs that were chosen to serve as exemplary illustrations. Thus, the scope of the present invention should not be limited to the specific illustrative structures described herein, but rather extends at least to the structures described by the language of the claims, and the equivalents of those structures. To the extent that there is a conflict or discrepancy between this specification as written and the disclosure in any document incorporated by reference herein, this specification as written will control.

What is claimed is:

1. An electronic hearing protection device configured to fit in the ear of a human user, comprising:
    an earpiece body configured to fit substantially in the cavum concha of a user's ear and configured to receive sound, to process the sound, and to emit processed sound through a speaker port;
    and,
    an eartip configured to fit into the ear canal of the user's ear, the eartip being detachably attached to the earpiece body and comprising a through-passage with a first, sound-receiving opening that is acoustically mated to the speaker port of the earpiece body and with a second, sound-emitting opening that faces toward the inner ear of the user,
        wherein the device is configured so that when the device is fitted in the ear of a user, the eartip externally occludes the ear canal and the earpiece body internally occludes the eartip, and
        wherein the earpiece body comprises a housing that exhibits an at least generally bilaterally symmetrical shape when viewed along a long axis of the eartip and that comprises at least one contact surface that is configured so that when the device is fitted in the ear of a user, the at least one contact surface of the housing contacts a skin surface of an ear component that defines at least a portion of a radially outer perimeter of the concha of the user's ear.

2. The device of claim 1 wherein the at least one contact surface of the housing is configured so that when the device is fitted in the ear of a user, the at least one contact surface of the housing contacts at least one of a skin surface of a tragus, an antitragus, and a portion of an antihelix that is proximate the antitragus, of the user's ear.

3. The device of claim 2 wherein the housing comprises at least first and second contact surfaces that are configured so that when the device is fitted in the ear of a user, the first contact surface contacts a first portion of a first skin surface of a first ear component that defines a first portion of the radially outer perimeter of the concha of the user's ear, and a second contact surface contacts a second portion of a second skin surface of a second ear component that defines a second portion of the radially outer perimeter of a concha of the user's ear, with the areas of contact between the first and second contact surfaces of the housing and the skin surfaces with which they are respectively in contact with, being spaced around the perimeter of the housing with a circumferential separation of at least about 120 degrees.

4. The device of claim 3 wherein the housing is configured so that when the device is fitted into the user's ear, the device is held in the ear at least in part by a compression fit of the housing of the earpiece body of the device, with at least any two of a tragus, an antitragus, and a portion of an antihelix that is proximate the antitragus, of the user's ear.

5. The device of claim 1 wherein no part of the earpiece body extends into the cimba concha of the user's ear.

6. The device of claim 1 wherein no part of the earpiece body extends outward of the cavum concha of the user's ear.

7. The device of claim 1 wherein the device provides a Noise Reduction Rating of at least about 18 dB.

8. The device of claim 7 wherein the housing is configured to at least substantially prevent the entry of ambient airborne sound into the interior thereof, and wherein the housing exhibits an Ingress Protection Rating of IP67.

9. The device of claim 8 wherein the housing does not comprise any unoccluded through-openings.

10. The device of claim 7 wherein the device contains an internal, rechargeable, non-removable battery that is located within the housing, and wherein the housing does not comprise a battery door.

11. The device of claim 7 wherein the earpiece body contains a speaker with a mating surface that is mated against a seating surface of a speaker housing of the housing of the earpiece body so as to at least substantially prevent any ambient airborne sound that may be in the interior of the housing, from passing through the speaker port of the housing.

12. The device of claim 11 wherein the mating surface of the speaker is indirectly mated against the seating surface of the speaker housing; and, wherein the speaker housing is integral with at least a major housing part of the housing of the earpiece body and wherein the speaker housing comprises a speaker housing conduit that is entirely defined by surfaces that are integral with the speaker housing; and, wherein the speaker housing conduit receives airborne processed sound from the speaker and allows the airborne processed sound to pass therethrough to reach the speaker port.

13. The device of claim 1 wherein the housing of the earpiece body comprises one or more electrical connections by which an internal, rechargeable, non-removable battery that is located within the housing can be charged.

14. The device of claim 1 wherein the through-passage of the eartip is an internal through-passage that is at least generally aligned with a long axis of the eartip.

15. The device of claim 14 wherein the internal through-passage of the eartip does not comprise any level-dependent sound attenuating physical feature.

16. The device of claim 1 wherein the eartip is a single piece of resiliently compressible organic polymeric material with a hardness of less than about 40 on a Shore A scale.

17. The device of claim 1 wherein the earpiece body comprises a microphone for receiving ambient airborne sound and for converting the ambient airborne sound into electronic signals, circuitry for processing the electronic signals, and a speaker for emitting the processed electronic signals as processed sound.

18. The device of claim 17 wherein the microphone is provided on an outward face of the housing of the earpiece body, in a location that is aligned radially on-axis with a long axis of the eartip within a distance of about 2 mm.

19. The device of claim 18 comprising a touch-sensitive switch located on an outward face of the housing of the earpiece body, in a location that is displaced radially off-axis from a long axis of the eartip a distance of at least about 4 mm.

20. A kit comprising at least two earpiece bodies of claim 1 in combination with at least four eartips of claim 1, at least some of the eartips being of different sizes from each other.

21. A kit comprising at least one device of claim 1, in combination with a charging unit configured to charge at least one internal battery of the earpiece body of the device.

22. The kit of claim 21, wherein the charging unit is a portable charging unit that comprises at least one internal battery and that does not require an external power source.

* * * * *